United States Patent [19]
Østensen et al.

[11] Patent Number: 5,980,460
[45] Date of Patent: *Nov. 9, 1999

[54] ULTRASOUND IMAGING

[75] Inventors: Jonny Østensen; Morten Eriksen; Lars Hoff; Sigmund Frigstad; Nils Sponheim; Knut Dyrstad, all of Oslo, Norway

[73] Assignee: Nycomed Imaging AS, Oslo, Norway

[ * ] Notice: This patent is subject to a terminal disclaimer.

[21] Appl. No.: 09/052,936

[22] Filed: Apr. 1, 1998

Related U.S. Application Data

[63] Continuation of application No. PCT/GB96/02413, Oct. 2, 1996, which is a continuation-in-part of application No. 08/538,286, Oct. 2, 1995, Pat. No. 5,601,085.

[51] Int. Cl.$^6$ ....................................................... A61B 3/00
[52] U.S. Cl. ............................................. 600/454; 600/458
[58] Field of Search .................................... 600/454, 455, 600/441, 456, 457, 465, 458, 443

[56] References Cited

U.S. PATENT DOCUMENTS

| | | |
|---|---|---|
| 4,803,990 | 2/1989 | Bonnefous et al. . |
| 5,135,000 | 8/1992 | Akselrod et al. . |
| 5,150,292 | 9/1992 | Hoffman et al. . |
| 5,329,929 | 7/1994 | Sato et al. . |

FOREIGN PATENT DOCUMENTS

WO91 15999  10/1991  WIPO .

OTHER PUBLICATIONS

Shung et al., 1990 Ultrasonics Symposium, 3: 1545–1548 (1990).

Primary Examiner—George Manuel
Attorney, Agent, or Firm—Bacon & Thomas

[57] ABSTRACT

Temporal variations in backscatter from an ultrasound contrast agent located in the vascular system and induced by movement of the scatterers are used to visualize the presence of contrast agent by determining areas where correlation between successive ultrasound images is poor. This low level of correlation from intravascular contrast agent movement permits distinction between stationary bulk tissue and moving bulk tissue since movement of the latter solid tissue scatterers is correlated.

8 Claims, No Drawings

ULTRASOUND IMAGING

CROSS REFERENCE TO RELATED APPLICATIONS

This application is a continuation of PCT/GB96/02413 filed Oct. 2, 1996, which is a continuation-in-part of application Ser. No. 08/538,286 filed Oct. 2, 1995, now U.S. Pat. No. 5,601,085.

This invention relates to ultrasound imaging, more particularly to methods of imaging the vascular system of a human or animal subject which permit generation of enhanced images of body tissues and fluids, e.g. blood.

It is well known that ultrasound imaging is a valuable diagnostic tool, for example in studies of the vascular system, which term used herein embraces both vasculature and microvasculature as well as tissue penetrated thereby. Specific applications include cardiography and studies of tissue microvasculature. Such imaging is based on penetration of ultrasound waves, e.g. in the frequency range 1–10 MHz, into the subject, the waves interacting with interfaces of body tissues and fluids. Contrast in an ultrasound image derives from differential reflection and absorption of the ultrasound waves at such interfaces. Thus, for example, reflected waves may be analysed to give "grey-scale" images representing such interfaces on an appropriate visual display unit; Doppler techniques may be used to evaluate blood flow, information regarding which may, for example, be superimposed in colour upon such a grey-scale image.

It has long been recognised that contrast agents may advantageously be used to increase the difference in acoustic properties between different tissues and/or fluids, such agents typically being administered by intravenous injection when vascular studies are to be performed. Numerous contrast agent formulations have been proposed over the last 25 years, including emulsions, solid particles, water-soluble compounds, free gas bubbles and various types of encapsulated gas-containing systems; it is, however, generally accepted that low density contrast agents which are easily compressible are particularly efficient in terms of the acoustic backscatter they generate, and particular interest has therefore been shown in gas-containing and gas-generating systems.

Representative examples of such systems include gas-containing microparticulate contrast agents, for example as described in US-A-4442843, EP-A-0122624, EP-A-0123235, DE-A-3834705, WO-A-9221382, WO-A-9300930, WO-A-9313802, WO-A-9313808 or WO-A-9313809; protein-encapsulated gas- or gas precursor-containing contrast agents such as Albunex® or as described in, for example, WO-A-9217213, WO-A-9406477 or WO-A-9501187; polymer- and other synthetic material-encapsulated gas- or gas precursor-containing contrast agents, for example as described in EP-A-0398935, EP-A-0458745, WO-A-9217212, WO-A-9317718, WO-A-9506518 or WO-A-9521631; systems employing gases selected to exhibit long term stability in vivo, for example as described in U.S. Pat. No. 5,413,774 or WO-A-9305819; and liposomal gas-containing systems, for example as described in U.S. Pat. No. 5,228,446 or U.S. Pat. No. 5,305,757. The contents of all of the foregoing documents are incorporated herein by reference.

Such contrast agents intended for administration by intravenous injection are typically designed to generate gas microbubbles having sizes in the range 1–10 $\mu$m or less, e.g. 1–7 $\mu$m, in order to ensure free passage through the capillary bed of the pulmonary system. Such microbubbles effectively act as point scatterers of ultrasound, and because of their random motion in fluids such as blood the backscatter which they generate will contain interference patterns due to interference between individual returning echoes. This phenomenon is termed speckle and typically produces a moving mottled effect in ultrasound images. The presence of such speckle is generally considered disadvantageous by virtue of the reduced image quality, and various techniques have been proposed for reducing speckle, for example as described in U.S. Pat. No. 5,409,007.

The present invention is based on the finding that temporal variations in the backscatter from an ultrasound contrast agent induced by movement of individual scatterers can be used as a valuable tool for detecting the presence of the agent, thereby permitting effective visualisation of contrast agent-containing tissue and/or fluids such a blood. The invention also facilitates discrimination between perfused and non-perfused tissue; thus lack of blood perfusion in particular tissue will be evident as lack of contrast, whilst subnormal perfusion will be indicated by delayed appearance of contrast following injection of contrast agent.

In principle any measurable function generated by the contrast agent may be employed, the presence of contrast agent being determined by analysis to detect areas where correlation between successive ultrasound images is poor, thereby denoting the presence of moving contrast agent moieties. It will be appreciated that such relative lack of correlation arising from intravascular contrast agent movement may readily be distinguished from bulk tissue movements since movement of solid tissue scatterers will be correlated.

Thus according to one aspect of the invention there is provided a method of imaging vasculated tissue of a human or non-human subject, said tissue containing an ultrasound contrast agent, which method comprises generating successive ultrasound images of said tissue, scanning a plurality of elements of each of said images for one or more image parameters, calculating correlation values in respect of said image parameter(s) for corresponding elements in said successive images, identifying any region or regions for which there is a change in said correlation values exceeding a defined level and generating a display of said region or regions.

Ultrasound images which may be used in accordance with the invention include two- and three-dimensional images, such as B-mode images of time-varying amplitude of the signal envelope, for example generated from the fundamental frequency of the emitted ultrasound pulse, from subharmonics or higher harmonics thereof or from sum or difference frequencies derived from the emitted pulse and such harmonics; images generated from the fundamental frequency or the second harmonic thereof are preferred. Other two-dimensional images include colour Doppler images and Doppler amplitude images. Individual scanlines may also be used, for example radiofrequency ultrasound scanlines, either as the original radiofrequency signal or after mixing or demodulation with a carrier frequency and/or filtering. The scanlines may be processed by any appropriate technique before they are used; thus, for example, Doppler-demodulated scanlines, rectified scanlines or the amplitude of scanlines may be used. It will be appreciated that the scanlines may be actual received scanlines or may be constructed from a two- or three-dimensional image. In general the images are preferably analysed in digital form. Changes in correlation between successive images, including scanlines, may, for example, be determined in time domain, frequency domain or intensity domain as appropriate.

To reduce the effects of movement, successive images of tissues such as the heart or kidney may be collected with the aid of suitable synchronisation (e.g. gating) techniques, for example analogous to those used in ECG or respiratory movement recordings.

By way of example of the method of the invention, a lack of intensity correlation factor $d_{i(l,k)}$ for pixel (l,k) between images i and i-1 may be determined from the relative difference in intensities $I_{i-1(l,k)}$ and $I_{i(l,k)}$ in pixel (l,k) in images i-1 and i by the formula (I)

$$d_{i(l,k)} = \omega d_{i-1(l,k)} + (1-\omega)\left|\frac{I_{i(l,k)} - I_{i-1(l,k)}}{I_{i(l,k)} + I_{i-1(l,k)}}\right|$$

where $\omega$ is a time or memory averaging factor such that $0<\omega 1$. Alternatively a similar correlation factor $d_{Ai(l,k)}$ can be determined from the absolute difference in intensities by the formula (II)

$$d_{Ai(l,k)} = \omega d_{Ai-1(l,k)} + (1-\omega)|I_{i(l,k)} - I_{i-1(l,k)}|.$$

It will be appreciated that the correlation factors will be large when intensity correlation from image to image is poor, so that $d_{i(l,k)}$ is large in the presence of moving contrast agent. This can be used to enhance visualisation of contrast agent, e.g. by displaying regions where $d_{i(l,k)}$ exceeds a threshold value, by displaying the value of $d_{i(l,k)}$ according to an intensity or colour coded scheme or by combining $d_{i(l,k)}$ with the original image, e.g. by displaying a weighted sum of the correlation value $d_{i(l,k)}$ and the original image. It may be advantageous first to average $d_{i(l,k)}$ over a region in space, e.g. a selected number of pixels, in order to improve the signal to noise ratio.

Alternatively, if a and b represent image intensities for corresponding two-dimensional areas in successive images, e.g. from rectangular arrays of a number of pixels, these areas having a centre point $(x_0, y_0)$ and a size of ±w pixels in the x and y directions, repeated calculations of an intensity correlation coefficient r may be made for a limited two-dimensional range $(\Delta x, \Delta y)$ using the formula (III)

$$r = \frac{\sum_{x=-w}^{w}\sum_{y=-w}^{w}(a_{x_0+\Delta x+x,y_0+\Delta y+y} - a_{mean})(b_{x_0+x,y_0+y} - b_{mean})}{\sqrt{\sum_{x=-w}^{w}\sum_{y=-w}^{w}(a_{x_0+\Delta x,y_0+\Delta y+y} - a_{mean})^2 \cdot \sum_{x=-w}^{w}\sum_{y=-w}^{w}(b_{x_0+x,y_0+y} - b_{mean})^2}}$$

where $$a_{mean} = \frac{\sum_{x=-w}^{w}\sum_{y=-w}^{w} a_{x_0+\Delta x+x,y_0+\Delta y+y}}{(2w+1)^2},$$

$$b_{mean} = \frac{\sum_{x=-w}^{w}\sum_{y=-w}^{w} b_{x_0+x,y_0+y}}{(2w+1)^2}.$$

These calculations permit identification of the local tissue movement vector, thereby allowing for elastic deformation of tissue. In the absence of moving intravascular contrast agent the peak value of r (i.e. $r_{max}$) is likely to be close to 1, but is reduced by the presence of contrast agent. The entire image may be scanned by varying $(x_0, y_0)$ and the resulting two-dimensional matrix of $r_{max}$ used to generate a display of the presence of intravascular ultrasound contrast agent, e.g. as a coloured or pseudo-coloured overlay image. It will be appreciated that r may be displayed in similar ways to those described above in respect of $d_{i(l,k)}$, with the modification that low values of r (in contrast to high values of $d_{i(l,k)}$) will be used.

The images may be spatially high pass filtered prior to the above-described calculations being made, in order to remove coarser tissue anatomical details while retaining the finer motion-induced variations in backscatter intensity, thereby enhancing the method's sensitivity in regions where tissue image details produce large grey-scale contrast. The use of high-pass filtered sets of images will also result in the values of $a_{mean}$ and $b_{mean}$ being close to zero, so that their calculation for each investigated region may be unnecessary, thereby speeding up the calculations.

One may also identify for each image elements such as pixels or groups of pixels which exhibit low correlation between their signal intensity and the signal intensity of adjacent elements, comparing results for successive images and generating a display of any regions where a threshold-exceeding change in correlation occurs.

It will be appreciated that correlation coefficients such as those disclosed above are dimensionless and that the calculations are inherently insensitive to absolute values. The method of the invention is accordingly insensitive to instrument parameters such as gain settings and to regional variations in image brightness and contrast introduced by instrumentation properties.

Alternatively one may calculate the sum of absolute differences in pixel intensities between an area in image b centred at $(x_o, y_o)$ and having a size of ±w pixels in the x and y directions and a corresponding area in image a with a motion connecting offset in the range $(\pm\Delta x, \pm\Delta y)$, further correcting for regional attenuation differences by substracting the differences in mean brightness. Thus an area $(x_o, y_o)$ in image b is assigned a value indicating the presence of contrast agent if the minimum value of the function $f_{(\Delta x, \Delta y)}$ given by formula (IV)

$$f_{(\Delta x,\Delta y)} = \sum_{y=-w}^{w}\sum_{x=-w}^{w} |a_{x_o+\Delta x+x,y_o+\Delta y+y} - b_{x_o+x,y_o+y}| - \left(\left|\sum_{y=-w}^{w}\sum_{x=-w}^{w} a_{x_o+x,y_o+y}\right| - \left|\sum_{y=-w}^{w}\sum_{x=-w}^{w} b_{x_o+x,y_o+y}\right|\right)$$

exceeds a threshold for all values of $\Delta x$ and $\Delta y$ in the defined range. The threshold may advantageously be selected to be sufficiently high to avoid system noise falsely being detected as contrast. The time interval between images a and b is preferably short so as to minimise motion artefact; as noted above gating to respiration, ECG or other cyclic motion-inducing effects may also be employed in this respect.

Where it is desired to determine changes in correlation in time domain one may, for example, use detection techniques involving correlation of successive radio-frequency ultrasound scanlines, e.g. analogous to those disclosed in U.S. Pat. No. 4,803,990, the contents of which are incorporated herein by reference. Such techniques permit compensation for tissue movement by shifting the scanlines along the time axis until maximum correlation is achieved. Remaining variance will therefore be a measure of the presence of moving ultrasound contrast agent.

The intercorrelation function $f_i$ between two radiofrequency lines $e_i$ and $e_{i+1}$ may be expressed by the formula (V)

$$f_i(t_0, u) = \int_{t_0}^{t_0+w} e_i(t)e_{i+1}(t-u)dt$$

where $t_o$ is the ultrasound time of flight to the start of the region of interest and w is the length of the time window defining the region of interest. One may therefore determine the value of u (i.e. $u_{max}$) which maximises $f_i(t_0,u_{max})$ for a selected region starting at $t_o$; the maximum value of $f_i(t_o, u_{max})$ may be used in combination with the total signal intensity or other parameters in respect of the same region for determining the presence of contrast. Thus low signal intensity may be interpreted as denoting blood without contrast agent, high signal intensity with high $f_i(t_0,u_{max})$ as denoting moving tissue without contrast agent and/or laminar flow of contrast agent-containing blood, and high signal intensity coupled with low $f_i(t_0,u_{max})$ as denoting tissue in which contrast agent is present and/or turbulent flow of contrast agent-containing blood.

It will be appreciated that in such techniques the pulse repetition frequency of the ultrasound beams may be adjusted to optimise detection of, for example, the presence of capillary flow and to discriminate this from tissue movement.

Correlation changes in time domain may also be determined by observing phase differences between returned echoes from adjacent sample volumes along the time axis of returned ultrasound echoes. Such phase differences will normally be substantially constant in non-contrast agent-containing tissue regions irrespective of tissue movement, whereas the presence of moving contrast agent moieties may be recognised from variations in phase difference with time. Such detection of moving contrast agent moieties, e.g. within the myocardium, may be based on signal analysis techniques analogous to Doppler signal processing. Account may be taken of differences between signals arising from tissue movement and signals from moving contrast agent moieties, since adjacent tissue regions will generally move with substantially the same velocity by virtue of the relative stiffness and low deformability of tissue, whereas contrast agent moieties within the same regions will move with different velocities owing to the fine structure of the microvasculature within the tissue. The presence of contrast agent may therefore be determined by analysis of the temporal correlation of the phase-difference signal, e.g. to generate a two-dimensional representation of temporal phase variation between tissue regions.

In such embodiments of the invention primary data acquisition from appropriate scanned regions such as parts of the heart may be effected in similar manner to that used to construct individual images such as scanlines in colour Doppler or power Doppler imaging modalities. Complex demodulation of data from radio frequency ultrasound scanlines may be used to produce vectors representing amplitude and phase for individual signal components corresponding to sample volumes at different tissue depths along the line of scanning; this permits generation of three-dimensional data sets for each image (matrix A), with axes representing (i) distance from the transducer (corresponding to depth of the tissue sample, (ii) soundbeam angle, and (iii) time. High pass filtering in time domain, e.g. with a cut-off frequency of $\geq 25$ Hz, may be used to remove artefactual echo components caused by reflections and reverberations from stationary elements.

A phase-difference signal between adjacent sample volumes along the depth axis may be extracted by processing the data set into a new matrix B, for example using the formula (VI)

$$B_{k,l,m} = \frac{2A_{k,l,m} \cdot \overline{A_{k,l,m+1}}}{|A_{k,l,m}| + |A_{k,l,m+1}|}$$

(where k, l and m respectively denote indices for angle, time and depth in the original matrix A), or any other formula generating a signal with appropriate phase properties. It will be appreciated that in formula (V) use of the complex conjugate $\overline{A_{k,l,m+1}}$ as a multiplier substracts the phase of adjacent samples along the depth axis, whilst division by the sum of absolute values conserves the overall magnitude of the signal. Contrast agent-free tissue may be expected to give vectors of constant angle and only slow variations in absolute value after this operation, whereas contrast agent-containing tissue will generate substantial high-frequency temporal variance of the vectors; high pass filtering of the dataset B, e.g. with a cut-off frequency of ca. 200 Hz, will therefore extract the desired information.

Calculation of the variance along the time axis may, for example, be effected using the formula (VII)

$$P_{k,m} = \sum_{l} (B_{k,l,m})^2$$

followed by logarithmic compression of the resulting matrix P in standard manner to generate a polar coordinate representation of a final B-mode image with contrast specific detection properties.

Changes in correlation by frequency domain methods may readily be based on parameters determinable in colour flow Doppler measurements, in particular spectral parameters of the Doppler signal, including signal power, mean frequency and bandwidth. Thus contrast agent-perfused regions will generate Doppler signals with a large ratio between bandwidth and mean frequency as a result of non-uniform movement of the scatterers coupled with non-uniform motion of blood through capillaries in such regions, this effectively representing a visualisation of lack of correlation between successive images of such regions.

Thus a Doppler signal exhibiting a large bandwidth:mean frequency ratio, together with strong signal power relative to blood backscatter level may be interpreted as denoting the presence of contrast agent-perfused tissue.

Multivariate methods such as principal component analysis, principal factor analysis, partial least square analysis or cluster analysis may, if desired, be used in conjunction with any of the above-described embodiments, permitting more comprehensive analysis of the ultrasound images. It will be appreciated that it may be preferable to analyse digitised image sequences stored on video or in other electronic storage media in preference to performing real time analyses of this nature.

A major advantage of the method of the invention is that whereas conventional ultrasound imaging requires that backscatter from a contrast agent must be stronger than backscatter from the surrounding tissue in order to register an intensity increase, the present method requires only that backscatter from the contrast agent be of the same order of strength as backscatter from surrounding tissue since this can be discounted by virtue of its high correlation between successive images. Consequently a smaller dose of contrast agent may be effective than is the case for systems based on conventional intensity imaging. Such lowered doses will decrease contrast-induced attenuation and so aid diagnosis of non-perfused or under-perfused tissues in deeply situated regions of the body.

The method of the invention may utilise any appropriate contrast agent, which will normally be administered by intravenous injection. Representative contrast agents which may be employed include any of the gas- or gas precursor-containing systems described hereabove.

The following non-limitative examples serve to illustrate the invention:

Preparation 1

Preparation of contrast agent 500.4 mg hydrogenated egg phosphatidylserine was added to 100 ml water containing 5.4% (w/w) of a mixture of propylene glycol and glycerol (3:10 w/w). The mixture was shaken and heated to 80° C. for five minutes, allowed to cool to room temperature, shaken again and left standing overnight prior to use.

50 ml of the resulting solution was transferred to a round-bottomed flask with a conical neck. The flask was fitted with a glass jacket having a temperature control inlet and outlet connected to a water bath maintained at 25° C. A rotor stator mixing shaft was introduced into the solution and to avoid gas leakage the space between the neck wall and the mixing shaft was sealed with a specially designed metal plug fitted with a gas inlet/outlet connection for adjustment of gas content and pressure control. The gas outlet was connected to a vacuum pump and the solution was degassed for one minute. An atmosphere of perfluoro-n-butane gas was then applied through the gas inlet.

The solution was homogenised at 23000 rpm for 10 minutes, keeping the rotor stator mixing shaft such that the openings were slightly above the surface of the liquid. A white coloured creamy dispersion was obtained, and was transferred to a sealable container and flushed with perfluoro-n-butane. The dispersion was then transferred to a separating funnel and centrifuged at 12000 rpm for 30 minutes, yielding a creamy layer of bubbles at the top and a turbid infranatant. The infranatant was removed and replaced with water. Centrifugation was then repeated twice at 12000 rpm for 15 minutes. After the last centrifugation, the supernatant was replaced by 10% (w/w) sucrose. 2 ml portions of the resulting dispersion were divided between 10 ml flat-bottomed vials specially designed for lyophilisation, and the vials were cooled to −47° C. and lyophilised for approximately 48 hours, giving a white fluffy solid substance. The vials were transferred to a vacuum chamber, and air was removed by a vacuum pump and replaced by perfluoro-n-butane gas. Prior to use, water was added and the vials were gently hand-shaken for several seconds, giving microbubble dispersions suitable as ultrasound contrast agents.

EXAMPLE 1 in vivo imaging of a dog kidney

An anaesthetised dog was given an intravenous injection of 2 ml of a gas-containing microparticulate contrast agent (e.g. as described in WO-A-93/17718). After a 30 second delay contrast effects were recorded using a Vingmed 750 ultrasound scanner at 5 MHz, with the transducer positioned above the location of the kidney. B-mode images were recorded at 0.5 second intervals. The images were post-processed by analogue to digital conversion into 180×180 pixel matrices. Subsequent calculations were performed using formula (III) above using a value of 5 for the parameter w. Correlation values of less than 0.7 were used to indicate perfusion. Perfused areas of the kidney were seen as distinct regions, appearing early in the cortical regions and later in the medulla.

EXAMPLE 2

In vivo imaging of a dog heart

An anaesthetised dog was given an intravenous injection of 2 ml of a contrast agent suspension according to Preparation 1. Several series of short axis images of the heart were acquired using a Vingmed CFM 750 ultrasound transducer at 5 MHz, imaging being synchronised with the ECG so that one image per heart cycle was acquired in late diastole. The left anterior descending artery was occluded in one series of images.

The images were digitised using an 8-bit analogue to digital converter, giving intensity levels from 0 to 255, and transferred to a computer. These images were processed according to formula (II) above, with the time-averaging w set to w=0.5, and pixels with $d_{Ai(l,k)}$>were assigned a red colour. Perfused regions of the heart were clearly observed as areas with red colour, whereas the non-perfused region had distinctly lower values of $d_{Ai(l,k)}$ and corresponding pixels could be assigned their unprocessed values.

EXAMPLE 3

In vivo imaging of a dog heart

The procedure of Example 2 was repeated except that the images were processed according to formula (IV) above where w=Δx=Δy=2. Pixels in image b for which $f_{(\Delta x, \Delta y)}$<18 when calculated over the range (±Δx, ±Δy) retained their original values, whereas pixels for which $f_{(\Delta x, \Delta y)} \geq 18$ for all values of Δx and Δy were assigned a colour to indicate contrast. Perfused myocardium was thus shown as a coloured image, whilst the non-perfused region was distinctly seen as a non-coloured area. Following release of the left anterior descending artery occlusion the whole myocardium was shown as coloured, confirming that the method of the invention may reliably distinguish between perfused and non-perfused tissue even in the presence of moderate attenuation.

EXAMPLE 4

In vivo imaging of a dog heart

Imaging was performed on the heart of an anaesthetised 20 kg mongrel dog both before and after injection of contrast agent according to Preparation 1 (3 μl perfluorobutane/kg body weight), using the same instrument settings on a modified Vingmed S5 scanner operating at 3 MHz. The scanning sector covered a region showing the left ventricle, anterior intraventricular septum and right ventricle, and imaging was performed from the left parasternal short axis position in late diastole. Data sets comprising 30 repeated ultrasound echoes in each of 32 discrete, equidistant and angularly spaced directions were collected at a rate of 500 Hz, in similar manner to that used to construct single images in colour Doppler and power Doppler imaging modalities. Complex demodulation of the thus-obtained radio-frequency data produced vectors representing the amplitude and phase of the signals; individual scanlines contained 55 such complex sample, each corresponding to about 0.8 mm tissue depth along the scanline. The resulting three-dimensional data set, with axes representing distance from transducer, soundbeam angle and time as generated by the repeated 500 Hz scanline collection, was high-pass filtered with a cut-off frequency of 25 Hz to remove artefactual echo components from chest-wall reverberations, and was then processed in accordance with formulae (VI) and (VII) as above and logarithmically compressed to generate a polar coordinate representation of a final B-mode image. The thus-obtained images clearly showed greater contrast agent-enhanced tissue echogenicity than corresponding images generated from unprocessed primary radio-frequency data.

EXAMPLE 5

Doppler in vivo imaging of a dog kidney

An anaesthetised dog is given an intravenous injection of 2 ml of a gas-containing microparticulate contrast agent (e.g. as described in WO-A-93/17718). After a 30 second delay contrast effects are recorded using an ultrasound scanner at 3.75 MHz, with the transducer positioned above the location of the kidney. The Doppler signal from the dog's kidney is recorded, digitised and transferred to a computer for post-processing. The total signal power, mean frequency and bandwidth are calculated from the Doppler signal.

Thresholds are imposed on the signal power and bandwidths, and regions where both these thresholds are exceeded are displayed. Perfuse areas in the kidney are seen as distinct regions.

We claim:

1. A method of imaging vasculated tissue of a human or non-human subject, said tissue containing an ultrasound contrast agent, which method comprises generating successive Doppler demodulated ultrasound images of said tissue, scanning a plurality of elements of each of said images for one or more signal parameters, calculating correlation values in respect of said signal parameters for corresponding elements in said successive images, identifying any region or regions for which there is a change in said correlation values exceeding a defined level and generating a display of said region or regions.

2. A method as claimed in claim 1 wherein said parameters are selected from Doppler signal power, Doppler mean frequency and Doppler bandwidth.

3. A method as claimed in claim 1 wherein a display is generated in respect of a region or regions exhibiting a combination of high Doppler signal power and high Doppler bandwidth.

4. A method as claimed in claim 1 wherein a gas-containing or gas precursor-containing ultrasound contrast agent is employed.

5. A method as claimed in claim 1 wherein correlation values are used in combination with total signal intensity or other image parameters in respect of the same elements to determine the presence of contrast.

6. A method as claimed in claim 1 wherein the display is stored using an electronic storage medium.

7. A method as claimed in claim 1 wherein an image in respect of the calculated correlation values is displayed.

8. A method as claimed in claim 7 wherein said image is displayed in combination with a further image generated using an alternative modality.

* * * * *